United States Patent [19]

Newman et al.

[11] Patent Number: 5,175,143
[45] Date of Patent: Dec. 29, 1992

[54] PERFUMERY MATERIALS

[75] Inventors: Christopher P. Newman, Canterbury; Karen J. Rossiter, South Ashford; Charles S. Sell, Aldington, all of England

[73] Assignee: Unilever Patent Holdings B.V., Rotterdam, Netherlands

[21] Appl. No.: 831,098

[22] Filed: Feb. 10, 1992

Related U.S. Application Data

[63] Continuation of Ser. No. 484,567, Feb. 26, 1990, abandoned, which is a continuation-in-part of Ser. No. 150,168, Jan. 29, 1988, abandoned.

[30] Foreign Application Priority Data

Jan. 29, 1987 [GB] United Kingdom ................. 8701961

[51] Int. Cl.$^5$ ............................................... A61K 7/46
[52] U.S. Cl. .................................... 512/12; 549/369; 549/333
[58] Field of Search .......................... 512/12; 549/369

[56] References Cited

U.S. PATENT DOCUMENTS 3,748,344 7/1973 McCloud et al. .................... 549/369

FOREIGN PATENT DOCUMENTS 276998 8/1988 European Pat. Off. .
1448458 9/1976 United Kingdom .
1545954 5/1979 United Kingdom .
1549213 7/1979 United Kingdom .

OTHER PUBLICATIONS

CA 66 (19):85739H (1966).
CA 71 (13):60044t (1969).
CA 72 (25):131393q (1970).
CA 77 (23):151474y (1972).
J.O.C. 1961, 26, 2247.
CA 79 (15):92066h (1973).
CA 86 (16):111089f (1977).
CA 94 (7):47170m (1981).
CA 96 (25):217307x (1982).
CA 104 (8):51857h (1985).
CA 53:13064 (1956).

Primary Examiner—Nicky Chan

[57] ABSTRACT

Novel perfumery chemicals having a cyclic acetal structure and providing a variety of perfume notes, especially amber, are described. They are prepared by reacting specified diols and aldehydes/ketones.

3 Claims, No Drawings

PERFUMERY MATERIALS

This is a continuation of application Ser. No. 07/484,567, filed on Feb. 26, 1990, now abandoned, which is a continuation-in-part of Ser. No. 07/150,168, filed on Jan. 29, 1988, now abandoned.

FIELD OF THE INVENTION

This invention relates to novel perfumery materials having a cyclic acetal structure and organoleptic properties. The novel materials within this class are of value in the preparation of perfume compositions of use in fabric washing formulations, toilet soaps and toilet preparations and air fresheners, as examples.

BACKGROUND TO THE INVENTION

There is a general requirement in perfumery for component materials providing a variety of perfume notes in a composition. The perfumery materials within the class described herein provide notes over a wide range of odours, in particular certain members of the series possess a surprising amber odour.

GENERAL DESCRIPTION OF THE INVENTION

The present invention provides a class of perfumery compounds of the general formula I

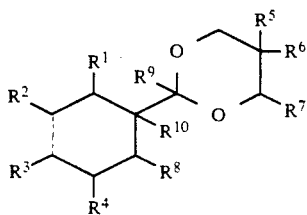

where the dotted line denotes a double or single bond within the cyclohexane ring and wherein R1, R2, R3 and R4 are each hydrogen or methyl R5 and R6 are each hydrogen, or a (cyclo) alkyl or (cyclo) alkenyl group containing 1 to 4 carbon atoms or an optionally substituted ring containing up to 5 carbon atoms or, together, form an optionally substituted ring containing up to 6 carbon atoms, including the carbon atom in the dioxane ring; R7 is hydrogen, methyl, ethyl, n-propyl, isopropyl, n-butyl, sec.butyl, isobutyl, tert.butyl; R8 and R9 are each hydrogen or methyl; R10 is hydrogen, methyl or isopropyl, with the proviso that the total number of C atoms is in the range 13 to 20, preferably 15 or more carbon atoms.

Examples of the groups defined by R5 and R6 are methyl, ethyl, propyl, isopropyl, n-butyl, isobutyl, tert.butyl, sec.butyl, vinyl, propenyl, isopropenyl, butenyl, isobutenyl, sec.butenyl, cyclopropyl cyclo butyl and, together, an optionally substituted cyclohex(en)yl ring.

These perfumery compounds are usable as odiferous components in perfume compositions. The amount of perfumery compound present will be dependent on the proposed use of the composition and will usually be at least about 0.1% by weight. The composition may contain up to about 10% or up to 95% by weight of at least one of the perfumery compounds described.

Preferred chemical compounds have R1, R2, R3, R4, R8 and R9 as defined above, R5 and R6 are each hydrogen, methyl, ethyl, sec.butyl, tert.butyl, n-propyl, isopropyl or a substituted hex-3-ene ring, R7 is hydrogen or n-propyl and R10 is hydrogen or methyl.

In this general formula no stereochemistry is implied. However it has been observed that odour character varies amongst the stereochemical isomers of some of the products of this invention. For example, products with the amber note generally demonstrate a stronger amber character in the more volatile stereoisomers. This effect is believed to be related to cis/trans isomerism about the dioxane ring. These isomers were separated for chemical and organo-leptic evaluation as pairs of diasteromers by glc and/or fractional distillation.

The perfumery compositions of the present invention are detectable and appreciated by the olfactory sense. Such compositions may be used as commercial products as they stand, eg. handkerchief perfumes, aftershaves and toilet waters or added to specific products, eg soaps, detergents, shampoos, skin creams, talcum powders, polishes and products releasing perfume into a space.

These cyclic acetals and ketals are conveniently formed by reacting a 1,3-diol of formula II with an aldehyde or ketone of formula III

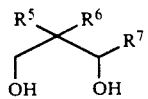

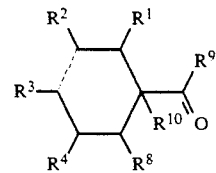

wherein the groups R1 to R10 inclusive are as defined in claim 1.

The 1,3-diol is preferably selected from the group 2-methyl-2-sec.butylpropane-1,3-diol, 2-methyl-2-propylpropane-1,3-diol, 2-ethylhexane-1,3-diol, 2-methyl-2-isopropylpropane-1,3-diol and 2-methyl-2-tert.butylpropane-1,3-diol.

The diols utilised in the preparation of the claimed compounds are obtainable from commercial sources or prepared using well characterised techniques. Thus the diols 2-methyl-2-isopropylpropane-1,3-diol; 2-methyl-2-tert.butyl-propane-1,3-diol and 2-methyl-2-(1-methylpropyl)propane-1,3-diol are prepared respectively from 3-methylbutanal, 3,3-dimethylbutanal and 3-methylpentanal by the following process. The appropriate aldehyde is subjected to a Mannich reaction with formaldehyde and diethylamine to introduce an alphamethylene group. The alkene bond in the product is hydrogenated at atmospheric pressure over 5% palladium on carbon. The saturated aldehyde so formed is treated with two equivalents of formaldehyde in the presence of a base. This gives the desired diol in a combined Aldol condensation and Canizzaro reaction.

Literature

GB 1549213 (Henkel) describes cyclic acetals and ketals used as inflammation inhibitors in cosmetic preparations. A number of acetals and ketals are listed in the passage on page 2 of the Henkel specification beginning at line 37. Some of the acetals and ketals disclosed are within the claim for novel compounds in the present application. The applicants claim the compounds previously defined in formula I, subject to the disclaimers that if the cyclohex(en)yl radical is substituted only by the dioxanyl group then R5 and R6 are not methyl if R7=isopropyl or propyl and R9=H R5 and R6 are not methyl if R7=isopropyl and R9=methyl R5 and R7 and R9 are not hydrogen if R6=Propyl R5 and R6 are not ethyl if R7 and R9=H and in addition excluding the specific compounds where R8 and R2 and R3 and R4 and R9 and R10=H, and R1 and R5 and R6 and R7=methyl R1 and R2 and R4 and R9 and R10 and R5 and R6=H and R3 and R7 and R8=methyl, The perfume compositions of the invention comprise a perfumery amount of a mixture of two or more perfumery materials according to Formula I or one or more of such materials with another fragrance material or mixture thereof. Such other fragrance materials and mixtures thereof which can be used in combination with the compounds of the present invention for the preparation of perfume compositions include natural products such as essential oils, absolutes, resinoids, resins, concretes, etc., but also synthetic fragrance materials such as hydrocarbons, alcohols, aldehyes, ketones, ethers, acids, esters, acetals, ketalas, nitriles, etc., being saturated or unsaturated, and aliphatic, carbocyclic or heterocyclic compounds.

Fragrance materials to be used in combination with the compounds according to the invention include geraniol, geranyl acetate, linalool, linalyl acetate, tetrahydro-linalool, citronellol, citronellyl acetate, dihydro-myrcenol, dihydro-myrcenyl acetate, tetrahydro-myrcenol, terpineol, terpinyl acetate, nopol, nopyl acetate, $\beta$-phenyl-ethanol, $\beta$-phenyl-ethyl acetate, benzyl alcohol, benzyl acetate, benzyl salicylate, benzyl benzoate, amyl salicylate, styrallyl acetate, dimethyl-benzyl carbinol, trichloromethyl-phenyl-carbinyl acetate, p-tert.butylcyclohexyl acetate, isononyl acetate, vetiveryl acetate, vetiverol, $\alpha$-hexyl-cinnamaldehyde, 2-methyl-3(p-tert.butylphenyl)-propanal, 2-methyl-3(p-isopropylphenyl)-propanal, 3-(p-tert.butylphenyl)-propanal, tricyclodecenyl acetate, tricyclodecenyl propionate, 4-(4-hydroxy-4-methylpentyl)-cyclohex-3-ene-carbaldehyde, 4-acetoxy-3-pentyl-tetrahydropyran, 3-carboxymethyl-2-pentylcyclopentane, 2-n-heptyl-cyclopentanone, 3-methyl-2-pentyl-cyclopentan-2-one, n-dodecenal, dec-9-enol, phenoxy-ethyl isobutyrate, phenyl-acetaldehyde dimethylacetal, phenyl-acetaldehyde diethylacetal, geranyl nitrile, citronellyl nitrile, cedryl acetate, 3-isocamphyl-cyclohexanol, cedryl methyl ether, isolongifolanone, subepine nitrile, aubepine, heliotropine, coumarin, eugenol, vanillin, diphenyl oxide, hydroxy-citronellal, ionones, methyl-ionones, iso-methyl-ionones, irones, cis-hex-3-enol and esters thereof, indan musks, tetralin musks, isochroman musks, macrocyclic ketones, macrolactone musks, ethylene brassylate, aromatic nitromusks.

Auxiliary agents and solvents that may be incorporated into perfume compositions containing the compounds according to the invention are e.g. ethanol, isopropanol, diethylene glycol monoethylether, diethyl phthalate, etc.

SPECIFIC DESCRIPTION OF THE INVENTION

Examples of the perfumery materials of the present invention and a process for their preparation will now be given to illustrate the invention.

EXAMPLE I

This example describes the preparation of the perfumery material which is a mixture of compounds in which i) R1, R3, R7, R8, R9 and R10 are hydrogen, R2, R4 and R5 are methyl and R6 is sec.butyl and ii) R2, R4, R7, R8, R9 and R10 are hydrogen; R1, R3, R5 are methyl and R6 is sec.butyl, and the dotted line represents a double bond in both cases.

A 3-necked round bottom flask (250 ml capacity) was fitted with a mechanical stirrer, thermometer and Dean and Stark apparatus, the latter was equipped with a double surface water condenser. Privetal (0.1 mole, 14.6 g) and 2-methyl-2-sec.butylpropane-1,3 diol (0.1 mole 14.6 g) were charged into the flask together with cyclohexane (50 ml) as solvent and a catalytic amount of p-toluenesulphonic acid (0.35 g). Privetal was a mixture of 2,4-dimethyl-and 3,5-dimethyl-cyclohex-3-ene-1-carboxaldehyde obtained from PPF International, Ashford, England; now obtained under the trade name Ligustral from Quest International, Ashford, Kent the successor company to PPF International. (The 1,3-diol was obtained from Hoechst GmbH of West Germany.)

The reaction mixture was heated under reflux at 90° C. and atmospheric pressure for 2.5 hours. At the end of this period no more water was removed as an azeotrope with the cyclohexane solvent. After cooling the mixture to ambient temperature, anhydrous sodium carbonate (0.5 g) was added to neutralise and dry the solution while stirring was continued for 1 hour. The mixture was then filtered and the solvent removed by evaporation at 30° C. under water pump vacuum. A 72% yield of crude product was obtained. The crude material was distilled using a 50 ml flask equipped with a Vigreux column (6.0×1.5 cm), a nitrogen bleed and a thermometer. The distillation was performed at a pressure of 6 mm of mercury and the desired mixture of acetals was collected over the temperature range of 135°–136° C. The yield of pure product was 50%.

GCMS showed the product to consist of several isomers with a relative molecular mass of 266. The cyclic acetal structures were supported by IR and proton NMR spectra.

This perfumery component has an intense and very persistent ambery character with woody or floral lily-like overtones.

The compounds prepared were:
2-(3,5-dimethyl-3-cyclohexen-1-yl)-5-methyl-5-(1-methylpropyl)-1,3-dioxane and
2-(2,4-dimethyl-3-cyclohexen-1-yl)-5-methyl-5-(1-methylpropyl)-1,3-dioxane.

EXAMPLE II

Example I was repeated using Privetal and 2-methyl-2-propylpropane-1,3-diol (obtained from Hoechst GmbH of West Germany).

The yield of the pure product, consisting of the isomers in which R1, R3, R7, R8, R9 and R10 are hydrogen, R2, R4 and R5 are methyl and R6 n-propyl, and R2, R4, R7, R8, R9, R10 are hydrogen, R1, R3, R5 are methyl and R6 is n-propyl and the dotted line in both cases represents a double bond was 80%. The product distilled over the temperature range 127° C. to 128° C. at 5 mm mercury.

This material possesses a novel and long-lasting green note with amber, sandalwood and earthy nuances.

The compounds prepared were:
2-(3,5-dimethyl-3-cyclohexen-1-yl)-5-methyl-5-propyl-1,3-dioxane and
2-(2,4-dimethyl-3-cyclohexen-1-yl)-5-methyl-5-propyl-1,3-dioxane.

EXAMPLE III

Example I was repeated using Isocyclocitral (a mixture of isomers of 2,4,6-trimethyl- and 3,5,6-trimethyl-cyclohex-3-ene-1-carboxaldehyde) as substitute for Privetal. Isocyclocitral is obtained from Quest International. The product was identical in structure to those of Example I except R8 is methyl and not hydrogen. The yield was 46%, the product distilled over the temperature range 135° C. to 140° C. at 0.5 mm mercury. This perfume material possesses a citrus/sulphurous note.

The compounds prepared were:
2-(3,5,6-trimethyl-3-cyclohexen-1-yl)-5-methyl-5-(1-methylpropyl)-1,3-dioxane and
2-(2,4,6-trimethyl-3-cyclohexen-1-yl)-5-methyl-5-(1-methylpropyl)-1,3-dioxane.

EXAMPLE IV

Example III was repeated using 2-methyl-2-propyl propane-1,3-diol and Isocyclocitral. The product was identical in structure to that obtained in Example II except R8 is methyl and not hydrogen. The yield was 71%, the product distilled over the temperature range 146° C. to 147° C. at 2 mm mercury. This perfume material has a note comparable with that of the Example II product material but has a lower intensity.

The compounds prepared were:
2-(3,5,6-trimethyl-3-cyclohexen-1-yl)-5-methyl-5-propyl-1,3-dioxane and
2-(2,4,6-trimethyl-3-cyclohexen-1-yl)-5-methyl-5-propyl-1,3-dioxane.

EXAMPLE V

Example I was repeated using 3-cyclohexene-1-carboxaldehyde (obtained from Degussa GmbH of West Germany) as equimolar substitute for Privetal. The product has R1, R2, R3, R4, R7, R8, R9 and R10 hydrogen, R5 methyl and R6 sec.butyl and the dotted line represents a double bond. The yield was 51%, the product distilled over the temperature range 134° C. to 138° C. at 1 mm mercury. This perfume material possesses a bitter grapefruit peel note.

The compound prepared was:
2-(3-cyclohexen-1-yl)-5-methyl-5-(1-methylpropyl)-1,3-dioxane.

EXAMPLE VI

The procedure of example I was repeated using equimolar quantities of Privetal and 2-ethyl hexane-1,3-diol (obtained from Hoechst GmbH). The product was a mixture i) R1, R3, R5, R8, R9 and R10 are hydrogen, R2 and R4 are methyl; R6 is ethyl and R7 is n-propyl ii) R2, R4, R5, R8, R9 and R10 are hydrogen; R1 and R3 are methyl; R6 is ethyl and R7 is n-propyl; in both isomers the dotted line is a double bond. The yield was 77%, the product distilled over the temperature range 138° C. to 142° C. at 4.5 mm mercury.

The material possesses a soft, clean, fresh, citrus peel note.

The compounds prepared were:
2-(3,5-dimethyl-3-cyclohexen-1-yl)-5-ethyl-4-propyl-1,3-dioxane and
2-(2,4-dimethyl-3-cyclohexen-1-yl)-5-ethyl-4-propyl-1,3-dioxane.

EXAMPLE VII

The procedure of example I was repeated using equimolar quantities of 1,3,5-trimethyl- and 1,2,4-trimethyl-cyclohex-3-ene-1-carboxaldehyde (prepared by Diels-Alder reaction of 2-methyl-1,3-pentadiene and methacrolein) and 2-methyl-2-sec.butylpropane-1,3-diol. The product was a mixture of isomers i) R1, R3, R7, R8 and R9 are hydrogen; R2, R4, R5 and R10 are methyl; R6 is sec.butyl and ii) R2, R4, R7, R8 and R9 are hydrogen; R1, R3, R5 and R10 are methyl; R6 is sec.butyl; in both isomers the dotted line is a double bond. The yield was 43%, the product distilled at 150° C. at 3.5 mm mercury.

The material possesses a smooth, weak, dry woody, ambery note.

The compounds prepared were:
2-(1,3,5-trimethyl-3-cyclohexen-1-yl)-5-methyl-5-(1-methylpropyl)-1,3-dioxane and
2-(1,2,4-trimethyl-3-cyclohexen-1-yl)-5-methyl-5-(1-methylpropyl)-1,3-dioxane.

EXAMPLE VIII

The procedure of example I was repeated using equimolar quantities of a mixture of 1-acetyl-3,5-dimethyl-cyclohex-3-ene and the 2,4-dimethyl isomer (prepared by Diels-Alder reaction of 2-methyl-1,3-pentadiene and methyl vinyl ketone) together with 2-methyl-2-sec.-butylpropane-1,3-diol. The product was a mixture of isomers i) R1, R3, R7, R8 and R10 are hydrogen; R2, R4, R5 and R9 are methyl and R6 is sec.butyl and ii) R2, R4, R7, R8 and R10 are hydrogen, R1, R3, R5 and R9 are methyl and R6 is sec.butyl; the dotted line is a double bond in both isomers. The yield was 61%, the product distilled over the temperature range 142° C. to 144° C. at 2 mm mercury.

The material possesses a sweet, honey, orange blossom note with light green undertones.

The compounds prepared were:
2-(3,5-dimethyl-3-cyclohexen-1-yl)-2,5-dimethyl-5-(1-methylpropyl)-1,3-dioxane and
2-(2,4-dimethyl-3-cyclohexen-1-yl)-2,5-dimethyl-5(1-methylpropyl)-1,3-dioxane.

EXAMPLE IX

The procedure of example VIII was repeated but using 2-methyl-2-propylpropane-1,3-diol as the diol reactant. The product was a mixture of isomers i) R1, R3, R7, R8 and R10 are hydrogen; R2, R4, R5 and R9 are methyl and R6 is n-propyl and ii) R2, R4, R7, R8 and R10 are hydrogen; R1, R3, R5 and R9 are methyl and R6 is n-propyl; in both isomers the dotted line is a double bond. The yield was 30%, the product distilled over the temperature range 120° C. to 121° C. at 4 mm mercury.

The material posseses a weak pleasant orris, orange-blossom note.

The compounds prepared were:
2-(3,5-dimethyl-3-cyclohexen-1-yl)-2,5-dimethyl-5-propyl-1,3-dioxane and
2-(2,4-dimethyl-3-cyclohexen-1-yl)-2,5-dimethyl-5-propyl-1,3-dioxane.

EXAMPLE X

The procedure of example VIII was repeated but using 2-ethylhexane-1,3-diol as the diol reactant. The product was a mixture of isomers i) R1, R3, R5, R8 and R10 are hydrogen; R2, R4 and R9 are methyl, R6 is ethyl and R7 is n-propyl and ii) R2, R4, R5, R8 and R10 are hydrogen; R1, R3 and R9 are methyl; R6 is ethyl and R7 is n-propyl; in both isomers the dotted line is a double bond. The yield was 17%, the product distilled over the temperature range 90° C. to 95° C. at 0.1 mm mercury.

The material possesses a weak, lactone, musky odour.

The compounds prepared were:

2-(3,5-dimethyl-3-cyclohexen-1-yl)-5-ethyl-2-methyl-4-propyl-1,3-dioxane and 2-(2,4-dimethyl-3-cyclohexen-1-yl)-5-ethyl-2-methyl-4-propyl-1,3-dioxane.

EXAMPLE XI

The procedure of example I was repeated using equimolar quantities of a mixture of 1,3,5- and 1,2,4-trimethyl-cyclohex-3-ene-1-carboxaldehyde (prepared as in Example 8) and 2-ethylhexane-1,3-diol. The product was a mixture in which i) R1, R3, R5, R8 and R9 are hydrogen, R2, R4 and R10 are methyl, R6 is ethyl and R7 is n-propyl, and ii) R2, R4, R5, R8 and R9 are hydrogen; R1, R3, and R10 are methyl; R6 is ethyl and R7 is n-propyl, in both isomers the dotted line is a double bond. The yield was 39%, the product distilled over the temperature range 100° C. to 105° C. at 0.1 mm mercury.

The material possesses a weak, fruity odour, reminiscent of apple, passionfruit and peach.

The compounds prepared were:

2-(1,3,5-trimethyl-3-cyclohexen-1-yl)-5-ethyl-4-propyl-1,3-dioxane and 2-(1,2,4-trimethyl-3-cyclohexen-1-yl)-5-ethyl-4-propyl-1,3-dioxane.

EXAMPLE XII

The procedure of example III was repeated using 2-ethylhexane-1,3-diol as the diol reactant. The product was identical in structure to that obtained in example VII except R8 is methyl and not hydrogen. The yield was 48%, the product distilled over the temperature range 130° C. to 135° C. at 6 mm mercury.

The material possessed an interesting myrrh note.

The compounds prepared were:

2-(3,5,6-trimethyl-3-cyclohexen-1-yl)-5-ethyl-4-propyl-1,3-dioxane and 2-(2,4,6-trimethyl-3-cyclohexen-1-yl)-5-ethyl-4-propyl-1,3-dioxane.

EXAMPLE XIII

This example describes the preparation of the perfumery material which is a mixture of compounds in which i) R1, R3, R7, R8, R9 and R10 are hydrogen; R2, R4 and R5 are methyl and R6 is sec.butyl and ii) R2, R4, R7, R8, R9 and R10 are hydrogen; R1, R3 and R5 are methyl and R6 is sec. butyl, and the dotted line denotes a single bond in both cases.

A 3-necked round bottom flask (100 ml capacity) was fitted with a mechanical stirrer, thermometer, gas inlet tube and gas outlet tube via a water condenser. The material as prepared in example I (0.05 mole, 13.3 g) was charged into the flask together with cyclohexane (40 ml) as solvent and a catalytic amount of platinum oxide (0.3 g $PtO_2$+water, 83% Pt, ex. Hopkin and Williams Ltd). The mixture was stirred vigorously and freed from dissolved oxygen by bubbling nitrogen through for fifteen minutes. The flow of nitrogen was then stopped and the system purged using hydrogen for 5 minutes. The system was shut off from the atmosphere and hydrogen was still admitted into the system using a gas meter to measure the volume of hydrogen consumed. The temperature rose from 20° C. to 35° C. during the first 25 minutes then fell slowly. After ca. 4 hours, uptake of hydrogen had ceased, a total of 1000 ml having been consumed. The supply of hydrogen was then shut off and the system purged by bubbling nitrogen through. The catalyst was removed by filtration under gravity and the solvent removed by evaporation at 30° C. under water pump vacuum. The crude material was distilled at a pressure of 0.1 mm mercury. The desired mixture of acetals was collected at 90° C. The yield of pure product was 46%.

GCMS showed the product to consist of several isomers with a relative molecular mass of 268. The cyclic acetal structures were supported by IR and proton NMR spectra.

The material possessed a green and ambery note reminscent of lily of the valley.

The compounds prepared were:

2-(3,5-dimethylcyclohexyl)-5-methyl-5-(1-methylpropyl)-1,3-dioxane and 2-(2,4-dimethylcyclohexyl)-5-methyl-5-(1-methylpropyl)-1,3-dioxane.

EXAMPLE XIV

The hydrogenation procedure of example XIII was repeated but using the product obtained from Example II. The product of hydrogenation was a mixture in which i) R1, R3, R7, R8, R9 and R10 are hydrogen, R2, R4 and R5 are methyl and R6 is n-propyl and ii) R2, R4, R7, R8, R9 and R10 are hydrogen, R1, R3 and R5 are methyl and R6 is n-propyl with the dotted line denoting a single bond in both compounds. The yield was 73%, the product distilled at 90° C. and a pressure of 0.1 mm mercury.

The materials posesses a weak woody note. The compounds were:

2-(3,5-dimethylcyclohexyl)-5-methyl-5-propyl-1,3-dioxane 2-(2,4-dimethylcyclohexyl)-5-methyl-5-propyl-1,3-dioxane.

EXAMPLE XV

Example I was repeated using Privetal and 2-methyl-2-tert.butylpropane-1,3-diol. The product was a mixture of isomers i) R1, R3, R7, R8, R9 and R10 are hydrogen; R2, R4 and R5 are methyl and R6 is tert-butyl and ii) R2, R4, R7, R8, R9 and R10 are hydrogen; R1, R3 and R5 are methyl and R6 is tert-butyl and the dotted line both cases represents a double bond. The yield was 57%, the product distilled at 110° C. and 0.2 mm mercury.

This material possesses an amber, woody character with almond top notes.

The compounds prepared were:

2-(3,5-dimethyl-3-cyclohexen-1-yl)-5-methyl-5-tert-butyl-1,3-dioxane and 2-(2,4-dimethyl-3-cyclohexen-1-yl)-5-methyl-5-tert-butyl-1,3-dioxane.

EXAMPLE XVI

Example I was repeated using Privetal and 2-methyl-2-isopropylpropane-1,3-diol. The product was a mixture of i) R1, R3, R7, R8, R9 and R10 are hydrogen; R2, R4 and R5 and methyl and R6 is isopropyl and ii) R2, R4, R7, R8, R9 and R10 are hydrogen; R1, R3 and R5 are methyl and R6 is isopropyl and the dotted line in both cases represents a double bond. The yield was 25%, the product distilled over the temperature range 90° C. to 95° C. at 0.2 mm mercury.

This material possesses fresh green, sappy and amber notes.

The compounds prepared were:
2-(3,5-dimethyl-3-cyclohexen-1-yl)-5-methyl-5-isopropyl-1,3-dioxane and
2-(2,4-dimethyl-3-cyclohexen-1-yl)-5-methyl-5-isopropyl-1,3-dioxane.

EXAMPLE XVII

Example I was repeated using a mixture of 1,1bis(hydroxymethyl)-3,5-dimethylcyclohex-3-ene and 1,1bis(hydroxymethyl)-2,4-dimethylcyclohex-3-ene (obtained by combined Aldol and Canizzaro rection of Privetal with two equivalents of formaldehyde in the presence of a base as described for the acyclic diols) as an equimolar substitute for the diol.

The yield of product, consisting of isomers in which:
i) R1, R3, R7, R8, R9 and R10 are hydrogen, R2, R4 are methyl and R5 and R6 together with the carbon of the dioxane ring to which they are attached form a 2,4-dimethylcyclohex-3-ene ring
ii) R2, R4, R7, R8, R9 and R10 are hydrogen, R1, R3 are methyl and R5 and R6 together (as above) form a 2,4-dimethyl cyclohex-3-ene ring
iii) R1, R3, R7, R8, R9 and R10 are hydrogen, R2, R4 are methyl and R5 and R6 together (as above) form a 3,5-dimethylcylohex-3-ene ring
iv) R2, R4, R7, R8, R9 and R10 are hydrogen, R1, R3 are methyl and R5 and R6 together (as above) form a 3,5-dimethycyclohex-3-ene ring and the dotted line in all cases represented a double bond, was 52%. The product was purified on a Leybold Heraeus wiped film evaporator with a jacket temperature of 95°–100° C. and internal pressure of 0.01 mm Hg.

This material posseses fruity and slightly herbal notes.

The compounds prepared were:
7,9-dimethyl-3-($2^1$,$4^1$-dimethyl-$3^1$-cyclohexen-$1^1$-yl)-2,4-dioxaspiro (5.5) undec-8-ene.
8,10-dimethyl-3-($2^1$,$4^1$-dimethyl-$3^1$-cyclohexen-$1^1$-yl)-2,4-dioxaspiro (5.5) undec-8-ene.
7,9-dimethyl-3-($3^1$,$5^1$-dimethyl-$3^1$-cyclohexen-$1^1$-yl)-2,4-dioxaspiro (5.5) undec-8-ene.
8,10-dimethyl-3-(3'5'-dimethyl-3'-cyclohexen-1'-yl)-2,4-dioxaspiro (5.5) undec-8-ene.

EXAMPLE XVIII

Any of the perfumery compounds exemplified above, or mixtures thereof, are used according to the invention with or without other fragrance materials as earlier described in effective amounts, as desired, to provide a variety of different perfume or perfumed preparations, e.g. handkerchief perfumes, aftershaves, toilet waters, soaps, shampoos, powders or the like. These may be formulated in conventional manner to contain up to 95%, preferably up to 10% by weight of the indicated mixture of perfumery materials.

We claim:

1. A perfume composition containing, as an essential odiferous component, an effective amount of at least one compound selected from the group consisting of 2-(3,5-dimethyl-3-cyclohexen-1-yl)-5-methyl-5-tert.butyl-1,3-dioxane; 2-(2,4-dimethyl-3-cyclohexen-1-yl)-5-methyl-5-tert.butyl-1,3-dioxane; 2-(3,5-dimethyl-3-cyclohexen-1-yl)-5-methyl-5-isopropyl-1,3-dioxane; 2-(2,4-dimethyl-3-cyclohexen-1-yl)-5-methyl-5-isopropyl-1,3-dioxane; 2-(3,5-dimethyl-3-cyclohexen-1-yl)-5-methyl-5-(1-methylpropyl)-1,3-dioxane; 2-(2,4-dimethyl-3-cyclohexen-1-yl)-5-methyl-5-(1-methylpropyl)-1,3-dioxane; 2-(3,5-dimethyl-3-cyclohexen-1-yl)-5-methyl-5-propyl-1,3-dioxane; 2-(2,4-dimethyl-3-cyclohexen-1-yl)5-methyl-5-propyl-1,3-dioxane; 2-(2,4-dimethylcyclohexyl)-5-methyl-5-(1-methylpropyl)-1,3-dioxane; and 2-(3,5-dimethylcyclohexyl)-5-methyl-5-(1-methylpropyl)-1,3-dioxane.

2. A perfume composition according to claim 1 containing at least about 0.1% by weight of at least one of said perfumery compounds.

3. A perfume composition according to claim 1 containing up to about 10% by weight of at least one of said perfumery compounds.

* * * * *